United States Patent [19]

Fischer et al.

[11] Patent Number: 5,480,779
[45] Date of Patent: Jan. 2, 1996

[54] CYCLOSPORINE ASSAY

[75] Inventors: Gunter Fischer, Halle; Namen G. Küllertz, Brandenburg, both of German Dem. Rep.

[73] Assignee: Arzneimittelwerk Dresden GmbH, Radebeul, Germany

[21] Appl. No.: 4,643

[22] Filed: Jan. 12, 1993

Related U.S. Application Data

[63] Continuation of Ser. No. 703,590, May 20, 1991, abandoned, which is a continuation-in-part of Ser. No. 398,092, Aug. 24, 1989, abandoned.

[30] Foreign Application Priority Data

Sep. 7, 1988 [DE] Germany ............... WPG01F/319577.4

[51] Int. Cl.$^6$ ............................. C12Q 1/37; C07K 5/00
[52] U.S. Cl. ............... 435/23; 435/18; 435/212; 435/213; 435/233; 436/512; 530/317; 530/330; 530/331
[58] Field of Search ............... 435/23, 18, 212, 435/213, 233; 436/512; 530/317, 330, 331

[56] References Cited

U.S. PATENT DOCUMENTS 4,592,997  6/1986  Wilhelms et al. ................... 435/23

OTHER PUBLICATIONS

G. Fischer, *Nature*, vol. 337, Feb. 2, 1989, pp. 476–478.
G. Fischer, *Biomed. Biochim. Acta* 43 (1984) 10, 1101–1111.
E. R. Schönbrunner, *J. Of Bio. Chem.*, vol. 266 (1991), pp. 1–2.
P. M. Kabra, *Clin. Chem.* 31/12, (1987), pp. 2272–2274.
R. K. Harrison, *Biochemistry*, vol. 29, No. 16 (1990), pp. 3813–3816.
H. P. Bächinger, *J. of Bio. Chem.*, vol. 262, No. 35 (1987), pp. 17144–17149.
P. A. Keown, *Trans. Pro.*, vol. XV, No. 4, Suppl. 1 (1983) pp. 2438–2441.
Woloszczuk, *Chemical Abstracts*, vol. 110, pp. 84, Ref. No. 166166y, 1989.
Takahashi et al, *Chemical Abstracts*, vol. 113, p. 318, Ref. No. 227149f, 1990.
Kofron et al, *Biochemistry*, vol. 30, No. 25, pp. 6127–6134, 1991.
Sigal et al, *J. Exp. Med.*, vol. 173, pp. 619–628, Mar. 1991.

*Primary Examiner*—Michael G. Wityshyn
*Assistant Examiner*—Abdel A. Mohamed
*Attorney, Agent, or Firm*—Schweitzer Cornman & Gross

[57] ABSTRACT

A process for determining the concentration of cyclosporine in a sample, which comprises adding to the sample a predetermined amount of an isomerase which isomerizes N-terminal peptide to proline, then measuring the enzyme-catalyzed inhibition of the isomerization of a proline-containing substrate, and determining the concentration or cyclosporine from a calibration curve.

10 Claims, 1 Drawing Sheet

CYCLOSPORINE ASSAY

This is a continuation of U.S. Ser. No. 703,590 filed on May 20, 1991, which was a continuation-in-part of U.S. Ser. No. 398,092, filed on Aug. 24, 1989, both now abandoned.

FIELD OF THE INVENTION

The present invention relates to a process for determining the concentration of cyclosporine and its biologically active derivatives.

BACKGROUND OF THE INVENTION

Determination of cyclosporine concentration in the body is important for supervision of therapy in patients treated with drugs which contain the therapeutically significant stripstance group of cyclosporines.

Cyclosporine is it cyclic polypeptide immunosuppressant agent consisting of eleven amino acids. It is usually produced as metabolite by the fungus species Tolypocladium inflatum Gams. Chemically cyclosporine is [R-{R*, R*-(E)}]-cyclic-(L-alanyl-D-alanyl-N-methyl-L-leucyl-N-methyl-L-leucyl-N -methyl-L-valyl-3-hydroxy-N-,4-dimethyl-L-2-amino-6-octenoyl-L-α-amino -butyryl-N-methylglycyl-N-methyl-L-leucyl-L-valyl-N-methyl-L-leucyl). Cyclosporine generally prolongs survival of allogencic transplants involving skin, heart, kidney, pancreas, bone marrow, small intestines, and lungs. It generally also suppresses some humoral immunity and to a greater extent cell-medicated reaction such as allograft rejection, delayed hypersensitivity, experimental allergic encephalomyelitis, Freund's adjuvant arthritis and graft vs. host disease in many animal species for a variety of organs.

Cyclosporine is the primary choice for prophylaxis of organ rejection in kidney, liver, and heart allogeneic transplants. They are generally always used with adrenal corticosteroids. The drug is also used in the treatment of chronic rejection in patients previously treated with other immunosuppressant agents. The use of cyclosporine presents a number of risks, and, therefore, its bioassay and prevention of excessive bioavailability are significant. In addition to the risk of anaphylaxis, when high doses are used, cyclosporine can also cause hepatotoxicity and nephrotoxicity. Furthermore, serum creatinine and BUN levels can also be unduly elevated during cyclosporine therapy. The aforementioned side effects are most often responsive to dosage reduction. Generally, cyclosporine therapy may require frequent dosage adjustment.

In some cases poor absorption can result in difficultly in achieving required therapeutic levels.

For all of the foreclosing reasons, in addition to renal and liver functions assessment by measurement of BUN, serum creatinine, serum bilirubin, and liver enzyme, also the frequent bioassay of cyclosporine is of paramount importance.

It is to be understood that any reference throughout the specification and the claims to "cyclosporine", is intended to cover cyclosporine as well as its biologically active and pharmaceutically acceptable derivatives and which behave in a biological sense as cyclosporine.

Cyclosporine concentrations have to be determined in aqueous systems, primarily in biological liquids, particularly in blood serum or plasma, synovial liquid, urine, suspensions of blood cells, homogenized tissue. etc.

It is necessary, to measure the concentration of the bioactive material in the body liquids of patients to establish the usual relatively narrow therapeutically logical concentration range of the medication and to eliminate immunological reaction of transplant rejection in the case of unduly small dosage, and also to eliminate toxic side effects when the dosage is too high. Furthermore, the necessity of such concentration determinations is especially indicated by the individual differences between patients and the natural metabolic rate and rate of elimination of the active ingredients, and the individual changes of elimination rate in the case of medications over a longer period, all of which require a differentiation in the dosage of the drug.

The customary concentration assay of cyclosporine is carried out by means of immunological or chromatographic techniques known per se, such as from Keown et al.: "The Clinical Relevance of Cyclosporine Blood Levels as Measured by Radioimmunossay", Transplant Proc. (1983), 15, pp 2438– 2441; and P. K Kabra, J. H. Wall, P. Dimson: "Automated Solid-Phase Extraction and Liquid Chromatography for Assay of Cyclosporine in Whole Blood". Clinical Chemistry (1987), 33, pp. 2272–2274.

The Keown et al. reference states that "Cyclosporine concentrations are measured both in serum, and in whole blood following erythrocyte lysis using the following two methods: (1) radioimmunoassay (RIA)—this was performed as described using the kit provided by Sandoz Limited Basel; (2) high-pressure liquid chromatography (HPLC)—this was performed using a Waters HPL chromatograph (Waters Associates, Bedford, Mass.), after acid and basic extraction to remove contaminating substances. The flow rate was 1.5 ml/min, and the CsA peak was read at 210 nm wavelength."

The Kabra article states that in this rapid, precise, accurate, cost-effective, automated liquid-chromatographic procedure for determining cyclosporine in whole blood, the cyclosprine is extracted from 0.5 mL of whole blood together with 300/µg of cyclosporin D per liter, added as internal standard, by using an Advanced Automated Sample Processing unit. The on-line solid-phase extraction is performed on an octasilane sorbent cartridge, which is interfaced with a RP-8 guard column and an octyl analytical column, packed with 5-µm packing material. Both columns are eluted with a mobile phase containing acetonitrile/methanol/water (53/20/27 by vol) at a flow rate of 1.5 mL/min and column temperature of 70° C. Absolute recovery of cyclosprorine exceeded 85% and the standard curve was linear to 5000/µg/L. Within-run and day-to-day CVs were >8%. Correlation between automated and manual Bond-Elut extraction methods was excellent (r=0.987). None of 18 drugs and four steroids tested interfered."

The immunological assays are based on the production of appropriate antibodies against the cyclosporine in question. The concentration of the antigen can be determined with the aid of such antibodies and available immunoassay techniques. A major problem of this method is that it requires a great deal of manual operation and the possibility of crossover reactions with therapeutically inactive compounds.

Chromatographic methods employ the separation by means of physical effects of the compound to be analyzed, from substances which would affect the accuracy of the determination. Therefore, the sensitivity of the analysis is strongly affected by the quality of the detector and also by the quality of the separation. A special drawback of this method is that relatively large amounts of material are required to determine the cyclosporine concentration e.g. in blood plasma, as well as the requirement for special apparatus.

DESCRIPTION OF THE INVENTION

The present invention provides a simple method for the quantitative determination of cyclosporines in humans medicated thereby, with high sensitivity and small sample requirement. The process of the present invention involves the adding to the sample such an amount of an isomerase enzyme which isomerizes peptide linkage N-terminally to proline that the enzyme activity achieves the range of about 10–90% of the level found in a reference solution devoid of cyclosporine, then measuring the inhibition of the enzyme-catalyzed isomerization of a proline-containing substrate, and determining the concentration of cyclospoine from a calibration curve. The process is carried out with a catalytically active peptidyl-prolyl cis-trans isomerase (PPlase) which is sensitive to cyclosporines (see Schönbrunner et al. *Jnal. of Bio. Chem.* Vol 266 (1991) p. 12). Schönbrunner et al. describes the catalytic activity of peptidyl-prolyl cis/trans isomerases (PPlases) as follows: "Peptidyl-prolyl cis/trans isomerases (PPlases catalyze the slow cis=trans isomerization of Xaa-proline peptide bonds in short synthetic peptides. This enzymatic activity was first detected and purified from porcine kidney by Fischer et al. (1984). Proline isomerization is widely accepted to be one of the rate-determining steps in protein folding (Brandts et al., 1975; Schmid and Baldwin, 1978; Schmid et al., 1986). Porcine PPlase accelerates such reactions in the refolding of several small proteins in vitro (Lang et al., 1987; Lang and Schmid, 1988; Lin et al., 1988; Fischer and Schmid, 1990). PPlase from porcine kidney is a cytosolic protein of 17-kDa molecular mass. Sequencing surprisingly revealed this protein to be identical with cyclophilin from bovine thymocytes (Takahashi et al., 1989; Fischer et al., 1989). Cyclophilin had been identified originally as the major high affinity binding protein for the immunosuppressive drug cyclosporin A (C&A) (Handschumacher et al., 1984); Harding et al., 1986). Cyclophilins are very widely distributed. They have been found in virtually all organisms and in different cell compartments such as the cytosol, mitochondria, the endoplasmic reticulum, and in the periplasm of *Escherichia coli* (Handschumacher et al., 1984; Danielson et al., 1988; Tropschug et al., 1988; Davis et al., 1989; Lightowlers et al., 1989; Kawamukai et al., 1989; Shieh et al., 1989; Schneuwly et al., 1989; Haendler et al., 1989; Dietmeier and Tropschug, 1990; Liu and Walsh, 1990). The various members of this protein family share a high degree of sequence similarity. Several cyclophilins have been shown to display prolyl isomerase activity when assayed with a synthetic oligopeptide (Davis et al., 1989, Tropschug et al., 1990).

In protein folding, the efficiency of porcine 17-kDa PPlase cyclophilin as a catalyst depends, among other factors on the accessibility of the respective proline-containing chain segments for the isomerase (Lang et al., 1987; Kiefhaber et al. 1990b, 1990c). The slow folding reactions of some proteins are not accelerated by this prolyl isomerase even though proline-controlled steps appear to be involved (Lang et al., 1987; Lin et al., 1988). Catalysis of folding is strongly inhibited by CsA (Fischer et al., 1989).

The cellular functions of cyclophilins and of their prolyl isomerase activity are still unknown. Here we address the question of whether or not the catalysis of slow, proline-controlled steps in protein folding is a general function of cyclophilins. In our investigation, we employ cyclophilins from pig, man, *Neurospora crassa, Sacchromyces cerevisae,* and from *Escherichia coli.* To evaluate their potential as catalysts of protein folding, we use ribonuclease T1 (RNase T1) as a model system. The refolding of this protein is dominated by the slow isomerization of two prolyl peptide bonds, both of which are accelerated by porcine PPLase (Fischer et al., 1989; Kiefhaber et al., 1990a, 1990b, 1990c). Our results indicate that all cyclophilins that were investigated do in fact catalyze the in vitro refolding model protein."

The proteolytic enzymes, for example α-chymotrypsin and thrombin from bovine plasma (sold by Serva, Heidelberg, Federal Republic of Germany), suitably at pH 7–8.5, ionic concentration of 0.05–0.5, and at 5°–25° C., function in identical manner as enzyme assistants for indicating the PPlase, by acting on the substrate of the type Xaa-Pro-Yaa, whereby a chromophoric residue becomes rapidly cleaved. Suc-Ala-Ala-Pro-Phe-4-nitroanilide (Seq. No. 2)(sold by Bachem Biochemica, Heidelberg, Federal Republic of Germany) is identical to Glt-Ala-Ala-Pro-Phe-4-nitroanilide (Seq. No. 2) for purposes of the assay.

The conditions known per se for isolating the various PPlase that are useful in accordance with the invention, are described in the prior art, for example, in G. Fischer et al., Biotaed. Biochim. Acta 43, pp. 1101–1111 (1989), and G. Fischer et al., Nature (London) 337, pp. 476–478.

The Fischer et al., article in Biomed Blochim. Acta states that "the rates of cis to trans interconversion of Glt-$(Ala)_n$-Pro-Phe-4-nitroanilides (n=1–3) were estimated by means of a two-step process with chymotrypsin as the transsubstrate cleaving activity.

> By the aid of this system, pig kidney and several other tissues contained demonstrable catalytic activity against the cis to trans interconversion of the proline containing peptides. The active protein fraction was purified 38-fold from pig kidney cortex by ammonium sulfate precipitation and a series of column chromatographic techniques. Activity was detected against the cis to trans interconversion of Glt-Ala-Pro-Phe-4-nitroanilide, Glt-Ala-Ala-Pro-Phe-4-nitroanilide (Seq. I.D. No. 2), and Glt-Ala-Ala-Ala-Pro-Phe-nitroanilide (SEQ. ID No. 5) to a different extent. No activity was found with Phe-Pro-4-nitroanilide. With respect to the substrate specificity, this enzyme must be classified as a peptidyl-prolyl cis-trans-isomerase. The enzyme was strongly inactivated by p-chloromercuribenzoate, sodium dodecylsulfate, $Hg^2$ and $Cu^2$ -ions, but was not inhibited be metal chelators, diisopropyl-phosphorofluoridate and chloroiosylamidophenylbutane."

The Fischer et al. article in Nature states that "PPlase was isolated from pig kidney cortex. After a 40 60% animonium sulphate fractionation the protein was applied on a Sephadex cation exchange solumn at pH 8.5 and eluted with a linear KCl gradient (0 0.4M). This was followed by gel filtration over Sephadex G 75 and chromatography on phenyl Speharose or Fractogel Tsk AF blue. The procedure resulted in a 780-fold purification and yielded material that migrated as a single 17K band on denaturing polyacrylamide gels under reducing conditions. The N-terminal sequence was determined by automated Fdman degradation using a 477A sequencer and an on-line 120A PHT analyser (both from Applied Biosystems). In addition to the 17K PPlase, additional active protein species can be isolated which differ in M, and isoelectric point. They will not be discussed further here."

PPlase are enzymes which can be determined from their changing the properties of a suitable peptide substrate of the Xaa-Pro-Yaa type in the presence of a suitable assisting proteolytic enzyme. Thus one can obtain with a spectrophotometer it from about 390 nm to about 410 nm a characteristic curve as a function of time. Suitably in these substrates Yaa is a chromogene group (see Bächinger, et al., *J. Biol. Cheml, Vol.* 262 (1987), pp. 17144–17145), such as phenylalanyl-4-nitroanilide, and Xaa is an aminoacyl- or peptidyl residue (see Harrison, et al., *Biochemistry*, vol. 29 (1990) pp. 3813–3816), such as, for example Suc-Ala-Ala.

The Bäichinger article in the Journal of Biological Chemistry states "peptidyl-prolyl cis-trans isomerase was extracted from pig kidney cortex and partially purified. Enzyme activity was monitored against the cis-trans isomerization of succinyl Ala-Ala-Pro-Phe-methylcoumaryl amide (SEQ. ID NO. 2) by means of a two-step using chymotrypsin as the trans cleaving activity."

The Harrison article in Biochemistry states "The substrates investigated were peptides of the general structure Suc-Ala-Xaa-Pro-Phe-N-nitroamidide (SEQ. ID NO. 6), where Xaa=Gly, Ala, Val, Leu, Phe, His, Lys, or Glu."The suitable protease can be, for example, chymotrypsin, thermitase, proteinase, thrombin, or human leukocyte elastase as an indicator system in the substrate for the determination of PPlase. The protease is employed under the standard conditions of pH, buffer composition, temperature, and ionic concentration, which are suitable for these proteolytic systems. A PPlase sensitive to cyclosporine, having a molecular weight of 17kD is determined by electrophoresis and colmnar filtration in a manner known per se, can be isolated for example, from pigs' kidneys in a manner known per se, such as described in G. Fischer, H. Bang, C. Mech, in *Biomed. Blochim. Acta* 43 pp. 1101–1111, (1984). This article has been discussed above.

A substrate solution is a solution of the substrate Glt-Ala-Ala-Pro-Phe- 4-nitroanilide (Seq. No. 1), in dimethylsulfoxide or in another suitable solvent.

Not all Xaa-Pro-Yaa peptides are suitable as substrates for PPlase, but only some of that structure are suitable for determination of cyclosporine, for example (Glt-Ala-Ala-Pro-Phe-4-nitroanilide (Seq. No. 1). The suitability of other suitable substrates of that type can be determined by routine experimentation.

The cyclosporine concentration can be obtained by comparing the activities of the measurements without cyclosporine (control) and measuring the PPlase activity with cyclosporine added (sample). In this manner also the body's own isomerase, as well as the isomerizing activities contained in the assay, can serve as a measure for the. cyclosporine level.

BRIEF DESCRIPTION OF THE DRAWING

The invention is further described with reference being had to the drawing, wherein.

DESCRIPTION OF PREFERRED EMBODIMENTS

Activity determination of PPlase as well as concentration determination of cyclosporine is described by way of two illustrative examples in which the concentration of the inhibitor is determined in an otherwise customary manner from a calibration curve using the inhibition percentage of an amount of added enzyme.

EXAMPLE 1

0.035 Molar N-2-hydroxyethylpiperazine-N'-2-ethanesulfonic acid (HEPES) is employed at pH 7.8. 24 mg triple crystallized, α-chymotrypsin from bovine plasma pancreas, sold by Boehringer Mannhelm, Federal Republic of Germany, is employed in 4.2 ml of the aforementioned buffer. The substrate is 14 mg Glt-Ala-Ala-Pro-Phe-NHNp (Seq. No. 1), in 10 ml dimethylsulfoxide. The PPlase is isolated from pigs' kidneys and has a specific activity of 500 µMol/min. mg. Calibration samples of 5, 8, 18, 30, 36 and 40 ng/ml cyclosporine-A each are added to a human blood plasma pool cornmingled from a plurality of healthy blood donors, and after 20 minute prior incubation of each, the reaction is carried out for each, at 5° C. Measurement takes place at 410nm on a recording spectrophotometer sold by Perkin Elmer Co., Norwalk, Conn. under Model No. 356. The following compositions are employed for the control and for the sample

| Ingredient | Sample | Control |
| --- | --- | --- |
| Buffer | 550 µl | 540 µl |
| Chymotrypsin solution | 100 µl | 100 µl |
| PPlase solution | 20 µl | — |
| Sample | 20 µl | — |
| Substrate solution | 50 µl | 50 µl |

The calculation involves a numerical analysis of the measured extinction values multiplied by the time (in the range of from about 10 seconds to about five minutes) according to the equation $$\ln\left(\frac{a}{(a-x)}\right) = k \times t$$

where "a" is the starting value extrapolated for the average time. The calculated value is converted into activity by the formula given below.

The activity is determined by calculating the first order reaction kinetic rate constants of the sample (k-sample), and the control (k-control); and by calculating the measured activity of the sample according to the formula $$\text{Activity} = \frac{k\text{-sample}}{k\text{-control}} - 1$$

Figure 1:
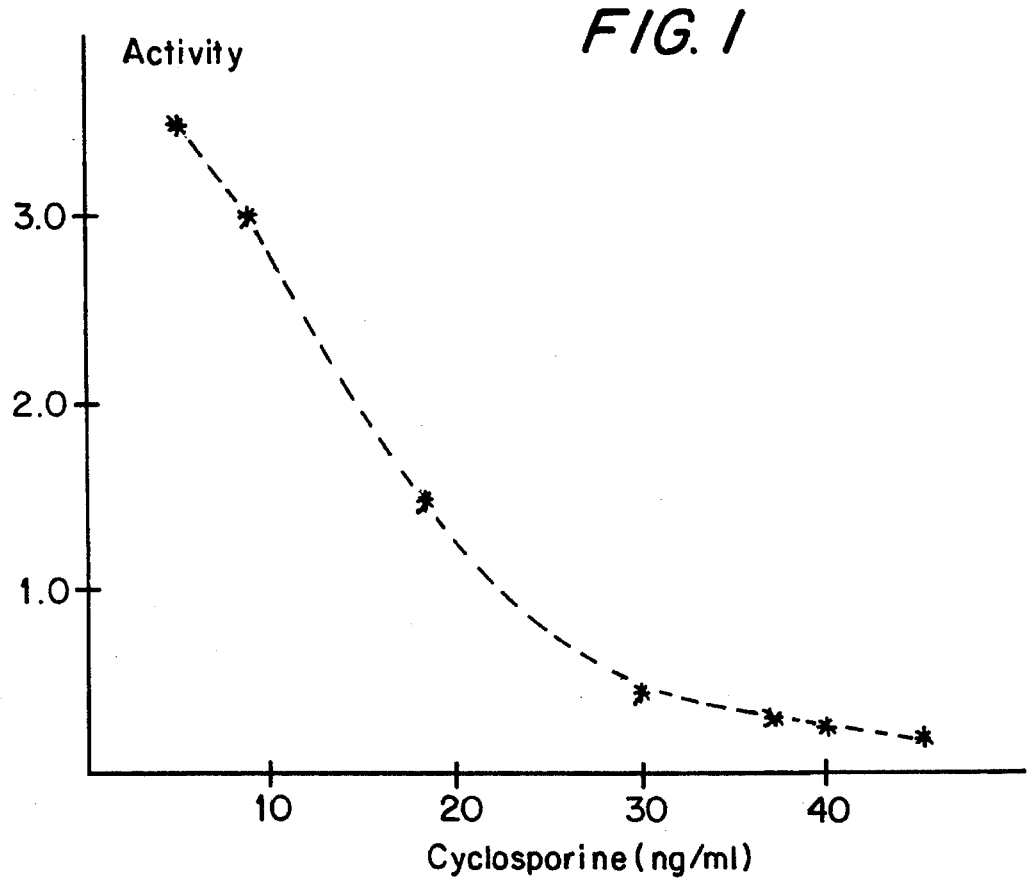
FIG. 1 is a calibration curve useful in connection with Example 1.

The unknown cyclosporine concentration is determined from the activity value on the ordinate of the calibration curve shown in FIG. 1.

EXAMPLE 2

Figure 2:
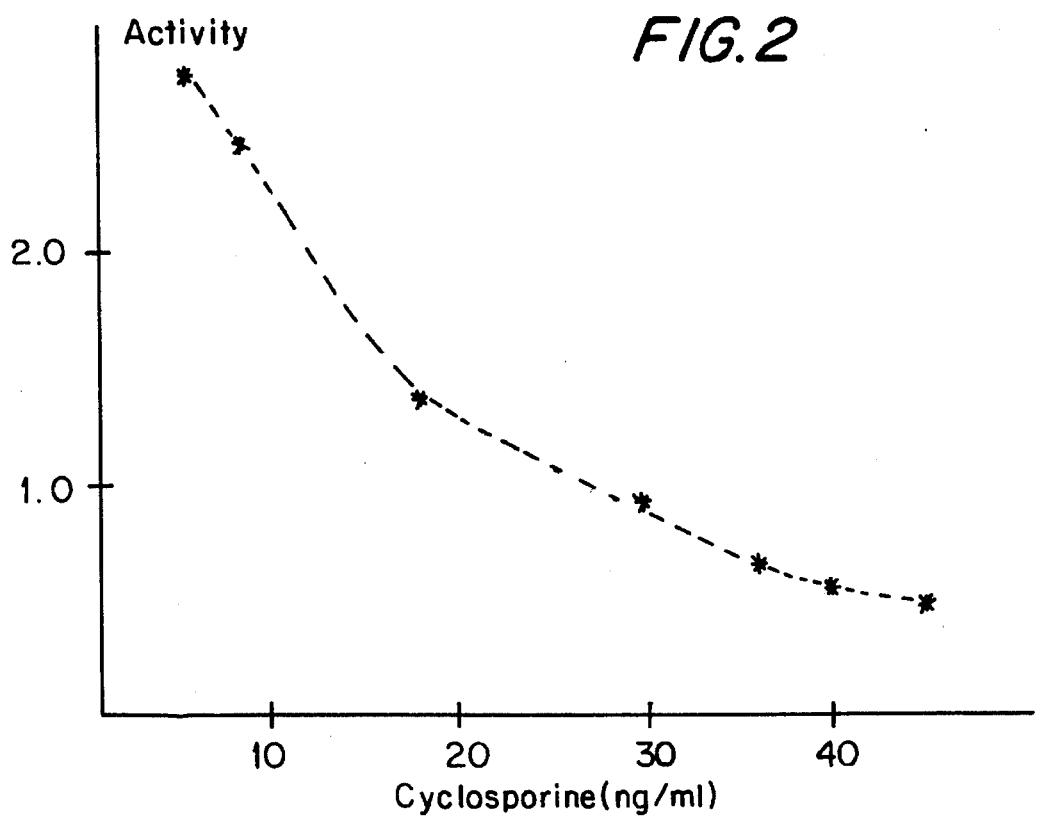
FIG. 2 is a calibration curve useful in connection with Example 2.

The same amount of buffer is used in Example 1, the same chymotrypsin, all in the same manner as in Example 1, except that the substrate is glutaryl-Ala-Pro-Phe-4-nitroanilide (Seq. No. 6). The cyclosporine concentration is determined by use of the calibration curve of FIG. 2.

EXAMPLE 3

The process is carried out as in Example 1, but instead of chymotrypsin and Glt-Ala-Ala-Pro-Phe-4-nitroanilide, (Seq. No. 1) 2.5 mg/ml subtilisin type VIII from *Bacillus*

*lichenoformis* obtained from Sigma Chemicals Deisenhofen, Federal Republic of Germany, is used as the protease, and 16 mg/10 ml dimethylsufoxide Suc-Ala-Ala-Pro-Met-4-nitroanilide (Seq. No. 3) obtained from (Bachem Biochemica, Heidelberg, Federal Republic of Germany, is used.

EXAMPLE 4

The process is carried out as in Example 1, but instead of chymotrypsin and Glt-Ala-Ala-Pro-Phe-4-nitroanilide, 13.5 mg/ml proteinase K from *Tritirachium album* obtained from Serva Feinbiochemica, Heidelberg, Federal Republic of Germany, is used as the protease, and 15 mg/10 ml dimethylsulfoxide of Suc-Ala-Ala-Pro-Leu-4-nitroanilide (Seq. No. 4) obtained from Bachem is used.

EXAMPLE 5

The process is carried out as in Example 1, but instead of the substrate Glt-Ala-Ala-Pro-Phe-4-nitronilide, (Seq. No. 1) 1.1 mg/1-ml of the fluorescent peptide Suc-Ala-Ala-Pro-Phe-7-amido-4-methylcoumarine (Seq. No. 2) obtained from Bachem, is used. This peptide is described in Enc. J. Biochem., Vol. 153, p. 37 (1985). The reaction is monitored on a fluorescence spectrometer from Hitachi Tokyo, Japan, Model F 3010, at an excitation wavelength of 380 nm and emission wavelength of 440 nm.

EXAMPLE 6

The process is carried out as in Example 1, but instead of chymotrypsin and Glt-Ala-Ala-Pro-Phe-4-nitroanilide, (Seq. No. 1) 10.8 mg/ml of thermitase prepared according to R. Kleine (1982) Acta Biol. Med. Germ. 41, 89–102 from *Thermoactinomyces vulgaris,* is used as the protease, and 12 mg/10 ml dimethylsulfoxide acetyl-Ala-Ala-Pro-Ala-4-nitroanilide (Seq. No. 7) obtained from Bachem, is used.

---

We claim:

1. A process for determining the concentration of cyclosporine in a cyclosporine containing sample, which comprises adding to the sample an amount of an isomerase enzyme which isomerizes a peptide linkage N-terminally to proline wherein the enzyme activity achieves the range of 10–90% of the level found in a reference solution devoid of cyclosporine, then measuring the enzyme-catalyzed isomerization of a proline-containing peptide substrate, and determining the concentration of cyclosporine on an axis of a calibration curve plotting enzyme activity as a function of cyclosporine concentration.

2. The process of claim 1, wherein the isomerizing enzyme is a peptidyl prolyl cis/trans isomerase characterized by specific cyclosporin A $IC^{50}$ inhibitability of about 10 nanomolar.

3. The process of claim 1, wherein the substrate is a compound of the type Xaa-Pro-Yaa, wherein Yaa is a chromogene group, C-terminal bonded to a peptide and Xaa is an aminoacyl group or a peptide residue.

4. The process of claim 3, wherein Yaa is phenylalanyl-4-nitroanilide, leucyl-4-nitroanilide, methionyl-4-nitroanilide, alanyl-4-nitroanilide, or a -7-amido-4-methylcoumarine derivative, and Xaa is Suc-Ala-Ala.

5. The process of claim 3 wherein the substrate is the peptide Suc-Ala-Ala-Pro-Phe- 7-amido-4-methylcoumarine (Seq. No. 2).

6. The process of claim 1, further comprising adding a protease inhibitor for the determination of peptidyl-prolyl cis-trans isomerase to the sample.

7. The process of claim 1, further comprising adding a protease indicator for the determination of of peptidyl-prolyl cis-trans isomerase the indicator being chymotrypsin, human leukocyte clastase, thermitase, thrombin, subtilisin type VIII, or proteinase K.

8. The process of claim 1, wherein the isomerase is the peptidyl prolyl cis/trans isomerase cyclophilin having a 17.8 kDa molecular weight, as determined by electrophoresis and columnar filtration, the substrate is a peptide of the type Xaa-Pro-Yaa wherein Yaa is a chromogene group, and Xaa is aminoacyl or peptidyl residue, and adding a buffer and a proteolytic enzyme to the sample.

9. The process of claim 8, wherein said proteolytic enzyme is chymotrypsin, thrombin, subtilisin type VIII, thermitase, human leucocyte elastase or proteinase K, and said buffer is N-(2-hydroxyethyl)piperazine-N'-2-ethanesulfonic acid.

10. The process of claim 9, wherein Yaa is a phenylalanyl-4-nitroanilide, methionyl-4-nitroanilide, leucyl-4-nitroanilide, alanyl-4-nitroanilide, or a -7-amido-4-methylcoumarine derivative.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 5 amino acid residues
        ( B ) TYPE: amino acid
        ( C ) STRANDEDNESS: single
        ( D ) TOPOLOGY: linear ( i i ) SEQUENCE DESCRIPTION: SEQ ID NO: 1:

Glu  Ala  Ala  Pro  Phe
        1                      5

( 2 ) INFORMATION FOR SEQ ID NO: 2:

( i ) SEQUENCE CHARACTERISTICS:
        ( A ) LENGTH: 4 amino acid residues
        ( B ) TYPE: amino acid
        ( C ) STRANDEDNESS: single
        ( D ) TOPOLOGY: linear ( i i ) SEQUENCE DESCRIPTION: SEQ ID NO: 2:

Ala  Ala  Pro  Phe
        1

( 2 ) INFORMATION FOR SEQ ID NO: 3:

( i ) SEQUENCE CHARACTERISTICS:
        ( A ) LENGTH: 4 amino acid residues
        ( B ) TYPE: amino acid
        ( C ) STRANDEDNESS: single
        ( D ) TOPOLOGY: linear ( i i ) SEQUENCE DESCRIPTION: SEQ ID NO: 3:

Ala  Ala  Pro  Met
        1

( 2 ) INFORMATION FOR SEQ ID NO: 4:

-continued ( i ) SEQUENCE CHARACTERISTICS:
    ( A ) LENGTH: 4 amino acid residues
    ( B ) TYPE: amino acid
    ( C ) STRANDEDNESS: single
    ( D ) TOPOLOGY: linear ( x i ) SEQUENCE DESCRIPTION: SEQ ID NO: 4:

Ala Ala Pro Leu
    1

( 2 ) INFORMATION FOR SEQ ID NO: 5:

( i ) SEQUENCE CHARACTERISTICS:
    ( A ) LENGTH: 5 amino acid residues
    ( B ) TYPE: amino acid
    ( C ) STRANDEDNESS: single
    ( D ) TOPOLOGY: linear ( x i ) SEQUENCE DESCRIPTION: SEQ ID NO: 5:

Xaa Xaa Xaa Pro Phe
    1                 5

( 2 ) INFORMATION FOR SEQ ID NO: 6:

( i ) SEQUENCE CHARACTERISTICS:
    ( A ) LENGTH: 4 amino acid residues
    ( B ) TYPE: amino acid
    ( C ) STRANDEDNESS: single
    ( D ) TOPOLOGY: linear ( x i ) SEQUENCE DESCRIPTION: SEQ ID NO: 6:

Ala Xaa Pro Phe
    1

( 2 ) INFORMATION FOR SEQ ID NO: 7:

( i ) SEQUENCE CHARACTERISTICS:
    ( A ) LENGTH: 4 amino acid residues
    ( B ) TYPE: amino acid
    ( C ) STRANDEDNESS: single
    ( D ) TOPOLOGY: linear ( x i ) SEQUENCE DESCRIPTION: SEQ ID NO: 7:

Ala Ala Pro Ala
    1